United States Patent [19]
Maissami

[11] Patent Number: 5,791,898
[45] Date of Patent: Aug. 11, 1998

[54] LIGHT PRISM FOR APPARATUS DENTAL FILLING

[75] Inventor: Fari Maissami, Hinsdale, Ill.

[73] Assignee: Denbur, Inc., Hinsdale, Ill.

[21] Appl. No.: 880,535

[22] Filed: Jun. 23, 1997

[51] Int. Cl.$^6$ .................................................. A61C 3/08
[52] U.S. Cl. .................................. 433/164; 433/29
[58] Field of Search ................... 433/29, 164, 226, 433/228, 229

[56] References Cited

U.S. PATENT DOCUMENTS

| | | | |
|---|---|---|---|
| 4,666,405 | 5/1987 | Ericson | 433/229 |
| 5,007,837 | 4/1991 | Werly | 433/29 |
| 5,030,093 | 7/1991 | Mitnick | 433/164 |
| 5,358,404 | 10/1994 | Schumacher | 433/164 |
| 5,423,677 | 6/1995 | Brattesani | 433/29 |
| 5,554,029 | 9/1996 | Kowalyk et al. | 433/29 |

*Primary Examiner*—John J. Wilson
*Attorney, Agent, or Firm*—Bell, Boyd, & Lloyd

[57] ABSTRACT

The present invention reveals an improved light-transmitting apparatus and methods for polymerizing light-hardening dental fillings of Class II resins. In the improved apparatus and methods, a magnified prism is constructed in the middle of a light-transmitting apparatus which transforms broad light from a light transmitting source to a concentrated light to the center of the focal point of the tip of the apparatus. The improved apparatus and methods permit the optionally connection of the light-transmitting apparatus to a light source.

16 Claims, 3 Drawing Sheets

LIGHT PRISM FOR APPARATUS DENTAL FILLING

BACKGROUND OF THE INVENTION

1. Field of the Invention

The present invention pertains to a magnified prism constructed in the middle of a light-transmitting apparatus which transforms broad light from a light transmitting source to a concentrated light to the center of the focal point of the tip of the apparatus. The concentration of light through the magnified prism inherently improves the means to condense the light of the apparatus for polymerizing light hardening dental fillings of Class II resins.

2. Description of the Related Art

In the past few years, the use of light cured dental resins has become increasingly common among dentists. The resins must be thoroughly cured in order to be hardened. As such, polymerization is necessary through inducing illumination of ultraviolet light intensely to the resins. It is difficult to polymerize an entire filling because the activating light has a restricted range within the filling material. The difficulty is compounded when preparing fillings of Class II type resin materials in premolars and molars to establish optimal contact with an adjacent tooth. This difficulty is due to the fact that these filling materials cannot be made to condense like amalgam which causes a mechanical interlocking of alloy particles within the filling material.

Thus, when amalgam is pressed into a cavity which is defined by a more or less resilient matrix band, the band is unable to spring back and deform the amalgam which retains the shape imparted to it during condensation, even though it is still plastic in texture. A resin or composite material, on the other hand, is deformed by the resiliency of the matrix band which results in an unsatisfactory contact. When using Class II resins for tooth preparation, the matrix band must be pressed against an adjacent tooth while the filling material is being polymerized in order to establish adequate contact.

There has previously been successfully provided a light-transmitting apparatus for preparing a dental filling of light-hardening material in which the apparatus is comprised of a light conductor for illuminating a filling material where one end of the light conductor is mounted to a light transmitting source.

The mounted light transmitting device, as described in U.S. Pat. No. 4,666,405, has been used as an adapted light transmitting device for preparing a dental filling of light-hardening material. Such a light transmitting adapter device is designed to be mounted on a light transmitting source in order to be pushed into the filling material. The light transmitting adapter is inserted into a fiber optic handpiece in order for the adapter to be held firmly in position on the fiber optic handpiece by friction or screwing. The adapter becomes an attachment for the fiber optic handpiece. The lower part of the adapter is conical and narrow to permit the insertion in a cavity.

Once the apparatus is mounted to a fiber optic handpiece, its lower tip is pressed into the filling material, and at the same time, against a matrix band which is pressed against an adjacent tooth. As light passes through the fiber optic handle through the adapter, the light will induce polymerization in those parts of the filling material which are illuminated. Also, deeper parts of the interior of the filling are illuminated by inserting the adapter into the filling material. Once the filling material has been polymerized, the adapter is removed from the filling, as well as from the fiber optic handpiece. The remainder of the restoration process can be done without the use of the adapter.

It is, therefore, an object of the present invention to maximize the light concentration of a light-transmitting apparatus in order to efficiently polymerize the filling material in the most apical part of a tooth preparation. The apparatus is preferably made with polycarbonate material and then diamond polished tooled in order that the apparatus not stick to the filling material. The present invention further provides methods for polymerization of Class II resins without the imperative of mounting a light-transmitting apparatus onto a fiber optic handpiece.

It is a further object of the present invention to allow the broad light from a light-transmitting source to travel into a magnified prism enclave in the apparatus in order to concentrate the light to a focal point of light energy at the tip of the apparatus. At the same time, the conical or elliptical shape of the tip of the apparatus is contoured to the natural anatomy of the Class II tooth restoration. As used herein, a magnified prism is defined as a transparent body that is bounded in part by two nonparallel faces, is used to disperse a beam of light, and has the power or capability of causing the light to become more intense, or to increase the light's significance.

It is also an object of the present invention to allow a dentist to place the apparatus into the prepared tooth without the necessity of mounting the apparatus onto a light transmitting source.

The concentration of light in the light transmitting apparatus is accomplished by constructing a magnified prism in the middle part of the apparatus where the prism can directly concentrate the light to the tip of the apparatus. The present invention allows the light to travel to the middle of the apparatus into the magnified prism where the light is concentrated to the tip of the apparatus. By concentrating the light to the middle of the apparatus, the light is transformed to burst with energy from its focal point. The burst of light energy to the focal point of the tip of the apparatus allows the dentist to achieve polymerization of Class II dental fillings faster and more efficiently.

SUMMARY OF THE INVENTION

The present invention discloses an improved light-transmitting apparatus and methods for polymerizing light-hardening dental fillings of Class II resins.

The improved light-transmitting apparatus comprises a magnified prism positioned in the middle of one end of a light conductor that is pointed in an apparatus for preparing a dental filling of light-hardening filling material, the apparatus comprising a light conductor for illuminating a filling material placed within a tooth, wherein one end of the light conductor, having its other end capable of being connected to a light source, is pointed and adapted to be pushed into the filling material such that it engages with a matrix band placed around the tooth and urges said matrix band against a contact point of an adjacent tooth.

In another aspect of the improved apparatus, the one end is an adapter for optional detachable mounting on a light source, at least the lower part of the conductor being formed of a light-transmitting material that cannot be bonded chemically to the filing material. In another aspect of the apparatus, at least the lower part of the conductor is formed of a polycarbonate material. In yet another aspect of the improved apparatus, at least the lower part of the conductor is diamond polished tooled. In other aspects of the improved apparatus, the one end of the light conductor is conical or elliptical shaped.

An improved method comprises employing a prism positioned in the middle of one end of a light conductor and optionally connecting the other end to a light source in a method of preparing a dental filing of light-hardening filling material in a tooth, the drilled-out tooth being filled with a light-hardening filling material, wherein one end of a light conductor, having its other end capable of being connected to a light source, is pushed into the filling material and the light source is activated to harden the deeper parts of the filling.

In another aspect of the improved method, the one end of the light conductor is pressed against a matrix band surrounding the tooth so that said matrix band in its turn is pressed against an adjacent tooth to provide approximal contact during hardening. In other aspects of the improved method, the one end of the light conductor is conical or elliptical shaped.

Another improved method comprises employing a magnified prism positioned in the middle of one end of a light conductor and optionally connecting the other end to a light source in a method of preparing a dental filling of light-hardening filling material in a tooth, the drilled-out tooth being filled with a light-hardening filling material, wherein one end of a light conductor, having its other end capable of being connected to a light source, is pushed into the filling material to transmit, concentrate and spread light in the deeper parts of the filling and is pressed against a matrix band surrounding the tooth so that the matrix band in its turn is pressed against an adjacent tooth to provide for approximal contact during hardening and the light source is activated to harden the deeper parts of the filing. In other aspects of this improved method, the one end of the light conductor is conical or elliptical shaped.

Another improved method comprises employing a magnified prism positioned in the middle of a light-emitting point portion of a pointed light conductor and optionally connecting the other end to a light source in a method of filling a drilled-out cavity in a tooth which is provided with a matrix band, the method comprising:

filling the cavity with a light-hardening filling material;

pressing into the filling the light-emitting point portion of a pointed light conductor, the other end of which is capable of being connected to a light source, such that the point portion becomes surrounded by filling material and the point becomes engaged with the matrix band and presses the matrix band against an adjacent tooth and such that simultaneously light being emitted from the point portion is transmitted into the surrounding filling material to harden the deeper portions thereof;

withdrawing the point portion from the filling material;

filling the resulting hole in the filling material with additional filling material; and illuminating such additional material to harden the same.

In other aspects of this improved method, the pointed light conductor is conical or elliptical shaped.

DETAILED DESCRIPTION OF THE PREFERRED EMBODIMENT

The apparatus of the present invention is an improvement of the apparatus disclosed in U.S. Pat. No. 4,666,405 (Ericson), the entire contents of which are hereby incorporated by reference and relied upon. The apparatus of the present invention uses light to its optimal source of energy for the illumination of light to the tip of the apparatus. At the same time, the conical or elliptical shape of the apparatus is contoured to the natural anatomy of the Class II tooth preparation. The conical or elliptical shape allows the dentist to achieve more realistic contact with and better polymerization in the tooth preparation. The concentration of light directed to the tip of the apparatus, as well as the contoured or elliptical shape of the apparatus resembling the natural anatomy of a Class II tooth preparation makes the restoration procedure more efficient and faster.

The methods of the present invention are also improvements of the methods disclosed in U.S. Pat. No. 4,666,405 (Ericson). Unlike the methods disclosed in U.S. Pat. No. 4,666,405, the methods of the present invention do not require the mounting of the apparatus onto a fiber optic handpiece. The dentist need not mount the light-transmitting apparatus to the light-transmitting source in order to achieve polymerization of Class II dental fillings. Instead, the dentist may place the apparatus in the proximal box with one hand, and with the other, illuminate the light through the apparatus.

Thus, the dentist can achieve polymerization of Class II dental fillings without the need to mount the light-transmitting adapter onto the fiber optic handpiece. In other words, mounting of the apparatus onto a fiber optic handpiece in order to obtain optimal approximal contact is not a requirement or an essential step of the present methods. The methods of obtaining polymerization of Class II type dental filling material in the approximal cavity without the mounting of the apparatus to a light source allow the dentist to obtain optimal approximal contact with an adjacent tooth.

A first aspect of the present invention comprises a magnified prism inside the tip in the middle of the apparatus. The prism directs the broad light from the light-transmitting source to a focal point that allows the light to be concentrated to a burst of energy at the tip of the apparatus. The prism which directs light straight to the center of the tip of the apparatus is formed in an enclave in the middle of the tip. Also, the contoured or elliptical shape of the tip of the apparatus resembles the natural anatomy of the Class II tooth restoration. The contoured or elliptical shape allows the dentist to obtain more life-like contact within the tooth preparation.

Figure 1:
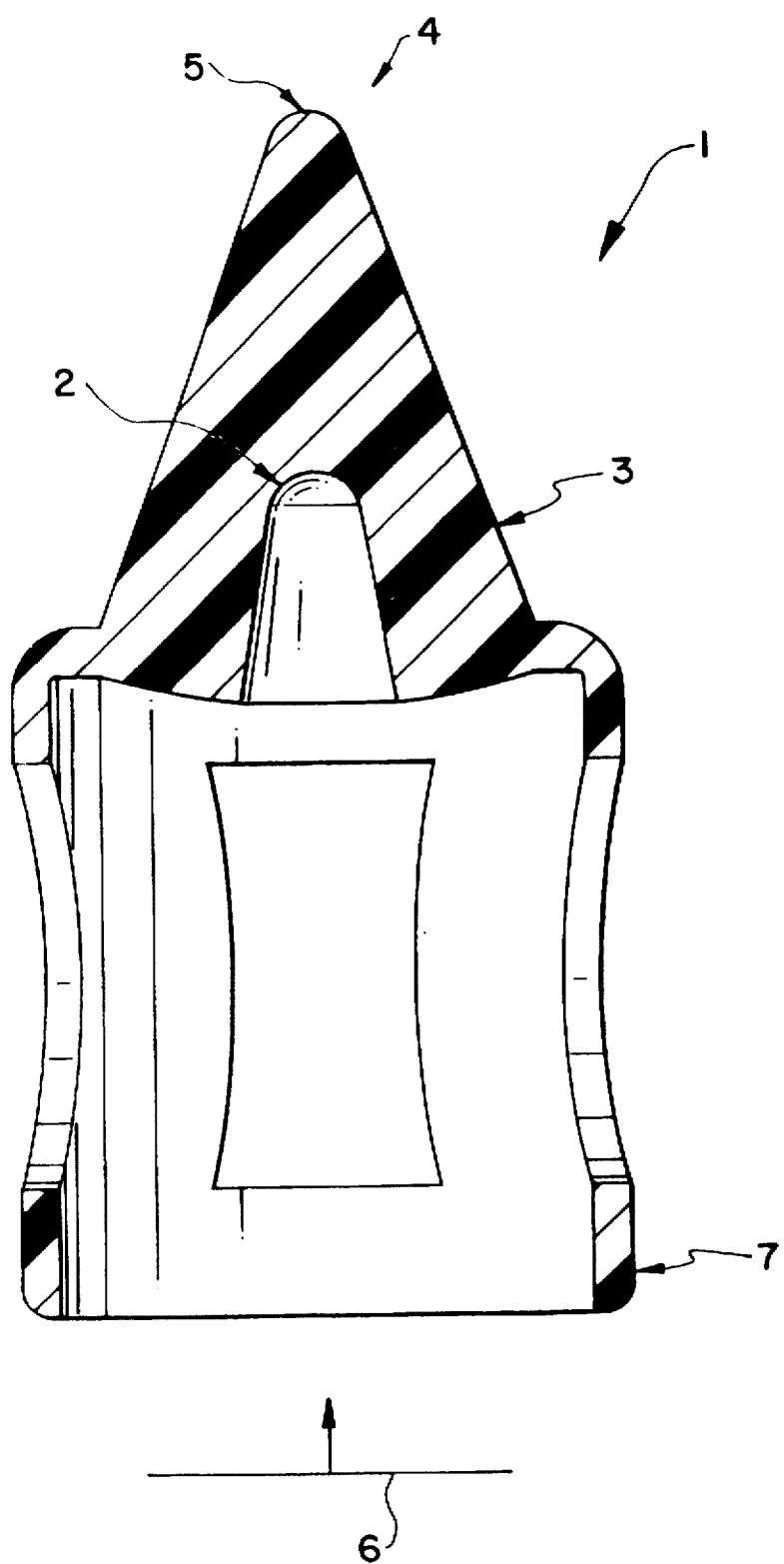
FIG. 1 shows a cross-section of one embodiment of the present invention, i.e., an improved conical shaped light-transmitting apparatus.
Figure 2:
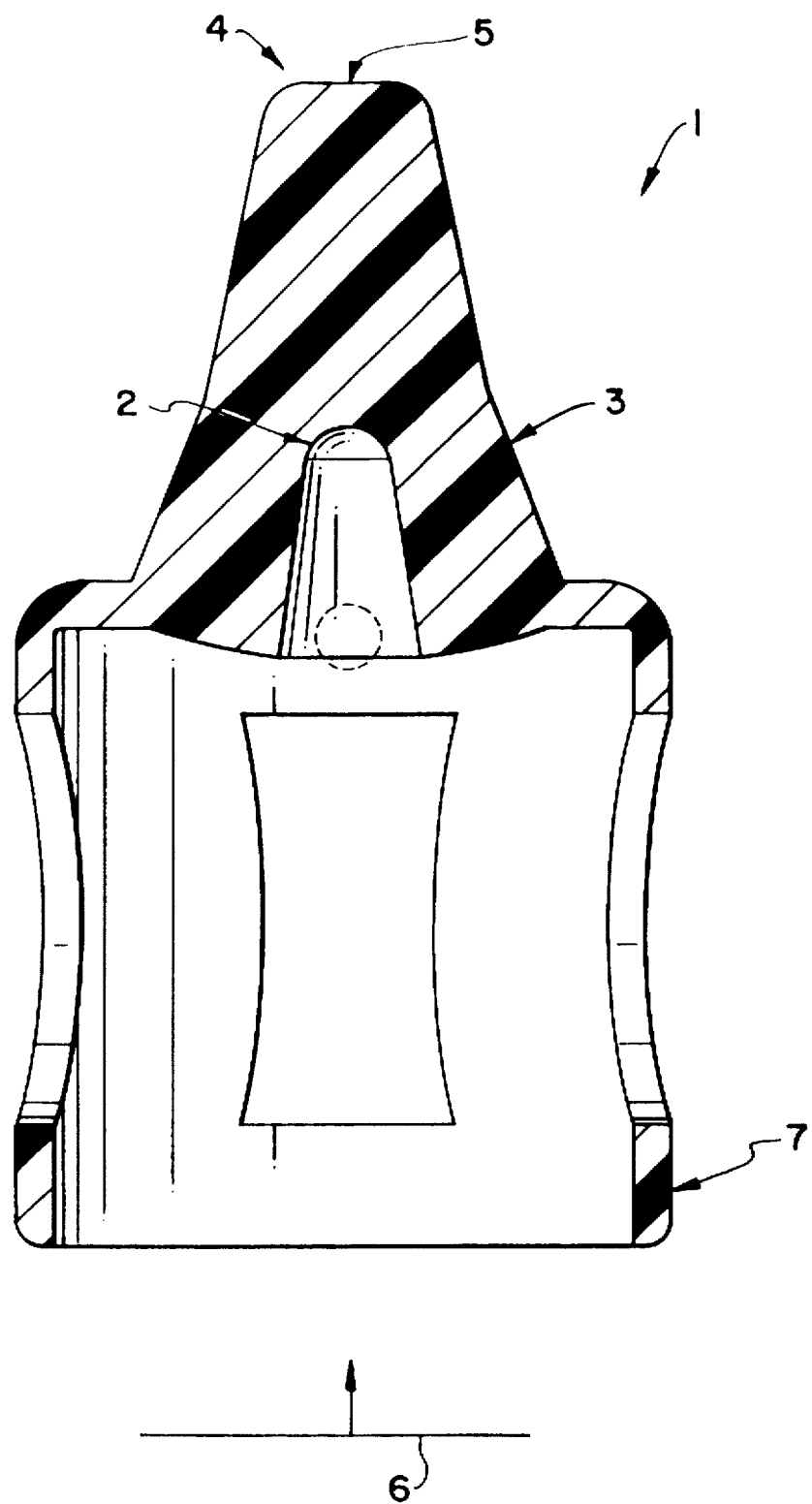
FIG. 2 shows a cross-section of another embodiment of the present invention, i.e., an improved elliptical shaped light-transmitting apparatus.

The following description illustrates the process of broad light entering the apparatus and exiting in a concentrated form of light at the focal point of the tip of the apparatus. Each of FIGS. 1 and 2 shows a cross-section of an embodiment of the improved light-transmitting apparatus or light conductor 1 of the present invention. The magnified prism 2 is shown in the middle of the tip 3 of the apparatus 1. The dotted line bisecting the cross-section denotes the central axis of the apparatus 1. The tip end or light-emitting point portion 4 of the apparatus is conical shaped (FIGS. 1 and 3) or elliptical shaped (FIGS. 2 and 4) to resemble the natural anatomy of the Class II tooth restoration. The focal point 5 of concentrated light is shown at the tip end 4 of the apparatus 1. The source of light 6 is shown entering the open adapter end 7 of the apparatus 1. The open adapter end 7 is capable of optionally being connected to a source of light 6.

Figure 3:
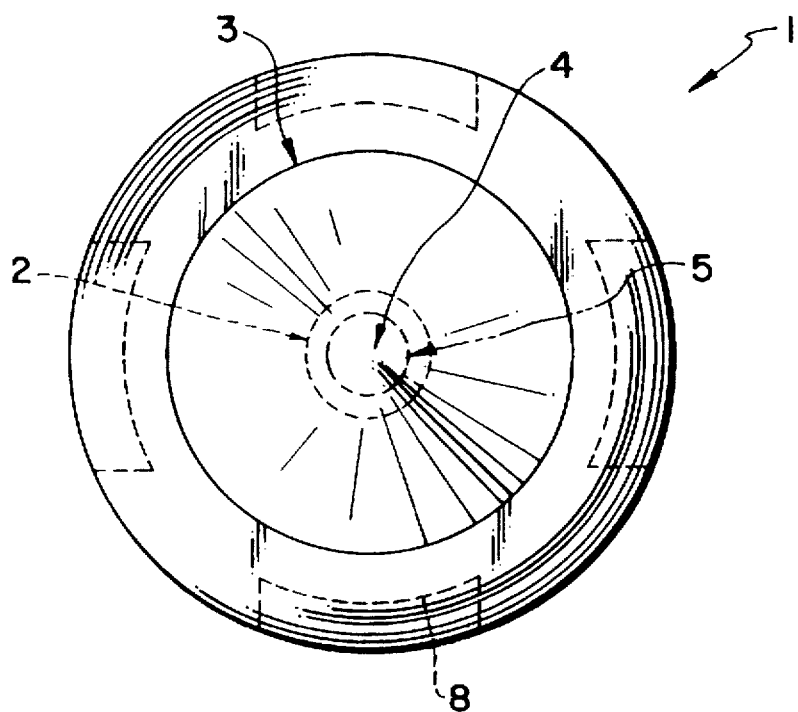
FIG. 3 shows a top perspective view of the improved conical shaped light-transmitting apparatus of FIG. 1.
Figure 4:
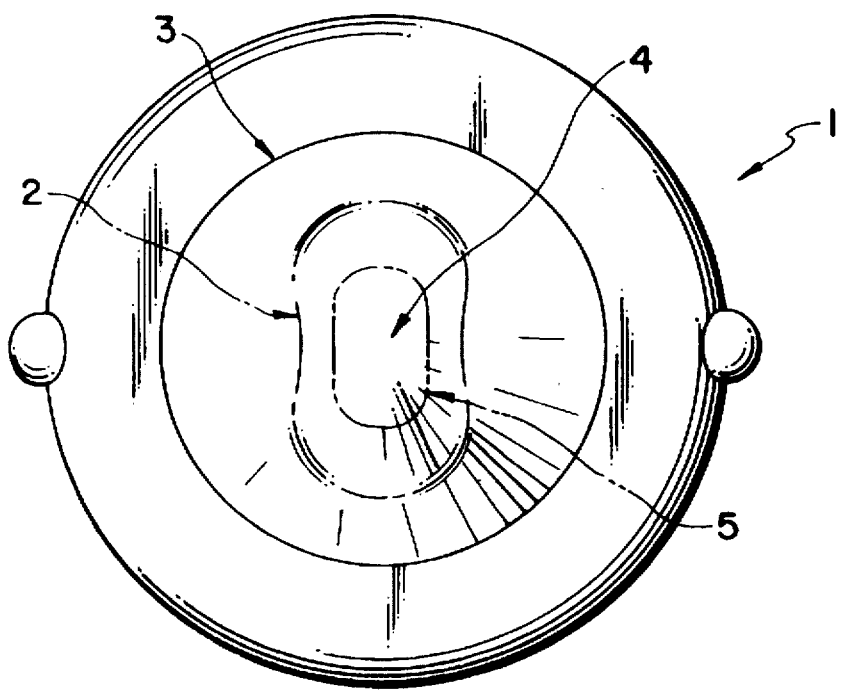
FIG. 4 shows a top perspective view of the improved elliptical shaped light-transmitting apparatus of FIG. 2.

Each of FIGS. 3 (conical shaped) and 4 (elliptical shaped) is a top perspective view of an embodiment of the improved light-transmitting apparatus 1. Again, the prism 2 is shown in the middle of the tip 3 of the apparatus 1. The focal point 5 of concentrated light is shown at the tip end 4 of the apparatus 1. Baskets 8 for optionally connecting the open adapter end 7 to a source of light 6 are shown on the periphery of the apparatus 1.

The use of the apparatus for allowing light to be concentrated to the focal point of the apparatus may be described as follows. Broad unconcentrated light 6 enters the apparatus 1 at the open adapter end 7 of the apparatus 1 and travels in the direction of the tip end 4. In the process, the light impacts or strikes the prism 2 located in the middle of the tip 3. The prism 2 focuses the beam of light along the central axis of the apparatus 1 in the direction of the tip end 4. At the tip end 4, the light exits from the apparatus 1 at its focal point 5. The light exits from the tip end 4 of the apparatus 1 from its focal point 5 converted into a concentrated light with a burst of energy.

EXAMPLE 1

A. THE PROBLEM

The fact is, to obtain satisfactory curing with a high conversion rate in light-curing composites, every part of the composite material has to be thoroughly and sufficiently irradiated by light in the proper wavelength range. The problem, however, is that the depth of cure is limited by the reduction in light intensity as light is attenuated by filling materials, tooth substance, and matrix system. Incomplete polymerization of the material may reduce the durability of the filling because of increased solubility and absorption. The biological compatibility of the material may also be affected due to release of unreacted resin.

The problem is further enhanced by the fact that proper curing is particularly difficult to achieve in the cervical area of the proximal box of Class II composite restorations. The proximal cervical surface is also difficult to inspect, to polish, and to clean. The composite material itself may be prone to plaque adhesion, leading to gingival reactions from cervical restorations. If the curing is deficient, corrosion of the surface may further promote plaque accumulation. Thus, the risk of development of secondary caries and gingival reaction will increase in an area already pre-disposed to such response.

B. THE SOLUTION

The solution is to get the light down efficiently to cure the cervical area of the proximal restoration. This is achieved with the apparatus and method of the present invention. The improved light-transmitting apparatus allows the light from a curing wand to concentrate in the tip of its cone from where it is distributed in a hemispheric fashion. The light is concentrated to the tip of the cone, illuminating with ultra high light in this area.

C. THE TECHNIQUE

An improved light-transmitting apparatus that fits curing wands with outer diameter of 7.7 to 8.2 mm is used. The apparatus is cold sterilized with a chemical disinfectant. Any conventional metal or plastic matrix band and any type of wedge may be used with the apparatus. When proceeding with a Class II tooth preparation, apply a small portion of resin to the proximal box. With the curing lamp switched off, insert or press down on the apparatus from the occlusal direction into the resin in the proximal box. Use the apparatus to hold the matrix in firm contact with an adjacent tooth. Now switch on the curing lamp. Maintain pressure for 40–60 seconds. Withdraw the apparatus when curing is complete. The procedure will form an arch of the cured resin in the proximal box, keeping the matrix in contact with the adjacent tooth. The rest of the restoration is completed without the use of the apparatus.

With the improved light-transmitting apparatus of the present invention, a totally tight proximal contact area is obtained easily and consistently. At the same time, resin in the depth of the proximal box is cured first due to concentration of light into deeper portion of the proximal box. This improves the curing of the cervical part of the composite, strengthening the filling and its resistance to chemical attack. It also reduces the contraction gap between the filling material and the cavity wall. Consequently, a significant increase in quality can be expected when Class II composite restorations are performed using the improved light-transmitting is apparatus of the present invention.

Care should be taken when pressing down the apparatus from the occlusal direction into the resin of the Class II proximal box. If pressed too far into the box, it may extrude between the matrix band and the tooth preparation, resulting in a poor cervical margin. Occasionally, some composite material may be displaced towards the occlusal cavity floor and cured without prior condensation. This may make it difficult to fill the occlusal part properly and eliminate air voids. Practice, however, will allow one to achieve excellent results in obtaining tight proximal contact in the cervical area every time.

EXAMPLE 2

The restorative procedure described in Example 1 is repeated except that an improved light-transmitting apparatus that fits curing wands with outer diameter of 8.7 to 9.2 mm is used.

EXAMPLE 3

The restorative procedure described in Example 1 is repeated except that an improved light-transmitting apparatus that fits curing wands with outer diameter of 9.3 to 9.7 mm is used.

EXAMPLE 4

The restorative procedure described in Example 1 is repeated except that an improved light-transmitting apparatus that fits curing wands with outer diameter of 12.0 to 12.4 mm is used.

The advantages of the improved light-transmitting apparatus and method of the present invention may be summarized as follows:

1. The present invention discloses the construction of a magnified prism in the middle of a light-transmitting apparatus which transforms broad light from a light transmitting source to a concentrated focal light. The concentration of light through the construction of the magnified prism inherently improves the means to concentrate the light of the apparatus for polymerizing light hardening dental fillings of Class II resins.

2. The concentration of light in the apparatus is achieved in the construction of a magnified prism in the middle part of the apparatus where the magnified prism is to directly concentrate the light to the tip of the apparatus. The invention of the magnified prism allows the light to travel to the middle of the apparatus where the light is concentrated to the tip of the apparatus.

3. The conical or elliptical shape of the tip of the apparatus contoured to the natural anatomy of the Class II tooth preparation allows the dentist to achieve realistic contact and better polymerization of the tooth preparation. This is due to the fact that the contoured or elliptical shape of the tip of the apparatus resembles life-like anatomy of the tooth preparation.

4. The method of the present invention allows polymerization of light hardening filling material in a tooth without the need of having the apparatus connected to a light transmitting source.

5. The method of the present invention allows the preparation of a dental filling of light hardening filling material in a tooth wherein the dentist places the apparatus into the proximal box with one hand and illuminates light through the apparatus with a light transmitting source with the other hand.

6. The method of the present invention further allows for improving the polymerization of Class II resins without the imperative of mounting the apparatus onto a fiber optic handpiece.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and scientific articles cited herein are hereby incorporated by reference in their entirety and relied upon.

What is claimed is:

1. In an apparatus for preparing a dental filling of light-hardening filling material, said apparatus comprising a light conductor for illuminating a filling material placed within a tooth, wherein one end of said light conductor, having its other end capable of being connected to a light source, is pointed and adapted to be pushed into the filling material such that it engages with a matrix band placed around the tooth and urges said matrix band against a contact point of an adjacent tooth, the improvement comprising a magnified prism positioned in the middle of said one end of said light conductor that is pointed.

2. The apparatus of claim 1, wherein said other end is an adapter for optional detachable mounting on a light source, at least the lower part of said conductor being formed of a light-transmitting material that cannot be bonded chemically to the filing material.

3. The apparatus of claim 2, wherein at least the lower part of said conductor is formed of a polycarbonate material.

4. The apparatus of claim 3, wherein at least the lower part of said conductor is diamond polished tooled.

5. The apparatus of claim 1, wherein said one end of said light conductor is conical shaped.

6. The apparatus of claim 1, wherein said one end of said light conductor is elliptical shaped.

7. In a method of preparing a dental filing of light-hardening filling material in a tooth, the drilled-out tooth being filled with a light-hardening filling material, wherein one end of a light conductor, having its other end capable of being connected to a light source, is pushed into the filling material and said light source is activated to harden the deeper parts of the filling.

the improvement comprising employing a magnified prism positioned in the middle of said one end of said light conductor and optionally connecting said other end to a light source.

8. The method of claim 7, wherein said one end of said light conductor is pressed against a matrix band surrounding the tooth so that said matrix band in its turn is pressed against an adjacent tooth to provide approximal contact during hardening.

9. The method of claim 7, wherein said one end of said light conductor is conical shaped.

10. The method of claim 7, wherein said one end of said light conductor is elliptical shaped.

11. In a method of preparing a dental filling of light-hardening filling material in a tooth, the drilled-out tooth being filled with a light-hardening filling material, wherein one end of a light conductor, having its other end capable of being connected to a light source, is pushed into the filling material to transmit and spread light in the deeper parts of the filling and is pressed against a matrix band surrounding the tooth so that said matrix band in its turn is pressed against an adjacent tooth to provide for approximal contact during hardening and said light source is activated to harden the deeper parts of the filing.

the improvement comprising employing a magnified prism positioned in the middle of said one end of said light conductor and optionally connecting said other end to a light source.

12. The method of claim 11, wherein said one end of said light conductor is conical shaped.

13. The method of claim 11, wherein said one end of said light conductor is elliptical shaped.

14. In a method of filling a drilled-out cavity in a tooth which is provided with a matrix band, said method comprising:

filling the cavity with a light-hardening filling material;

pressing into the filling the light-emitting point portion of a pointed light conductor, the other end of which is capable of being connected to a light source, such that the point portion becomes surrounded by filling material and the point becomes engaged with the matrix band and presses the matrix band against an adjacent tooth and such that simultaneously light being emitted from the point portion is transmitted into the surrounding filling material to harden the deeper portions thereof;

withdrawing the point portion from the filling material;

filling the resulting hole in the filling material with additional filling material; and illuminating such additional material to harden the same, the improvement comprising employing a magnified prism positioned in the middle of said light-emitting point portion of a pointed light conductor and optionally connecting said other end to a light source.

15. The method of claim 14, wherein said pointed light conductor is conical shaped.

16. The method of claim 14, wherein said pointed light conductor is elliptical shaped.

* * * * *